(12) United States Patent
Mitchell

(10) Patent No.: US 7,867,184 B2
(45) Date of Patent: Jan. 11, 2011

(54) SYSTEM AND METHOD FOR CORRECTING CLUBFOOT PROBLEMS IN CHILDREN

(76) Inventor: John R. Mitchell, 202 N. Madison, Box 125, Wayland, IA (US) 52654

(*) Notice: Subject to any disclaimer, the term of this patent is extended or adjusted under 35 U.S.C. 154(b) by 456 days.

(21) Appl. No.: 11/566,470

(22) Filed: Dec. 4, 2006

(65) Prior Publication Data

US 2007/0142760 A1 Jun. 21, 2007

Related U.S. Application Data

(63) Continuation-in-part of application No. 10/708,808, filed on Mar. 26, 2004, now Pat. No. 7,267,657.

(60) Provisional application No. 60/767,049, filed on Feb. 28, 2006.

(51) Int. Cl.
*A61F 5/00* (2006.01)
*A61F 5/37* (2006.01)
*A61F 5/14* (2006.01)

(52) U.S. Cl. .......................... 602/29; 128/882; 36/140

(58) Field of Classification Search .................. 602/28, 602/29, 1, 5, 23, 27; 128/869, 882; 36/140, 36/109, 89, 90, 45, 58
See application file for complete search history.

(56) References Cited

U.S. PATENT DOCUMENTS

| | | | |
|---|---|---|---|
| 2,585,342 A | 2/1952 | Morgan | |
| 2,906,261 A * | 9/1959 | Craig | ........................... 602/24 |
| 3,171,407 A | 3/1965 | Rogers | |
| 3,523,526 A | 8/1970 | Phelps | |
| 3,777,747 A * | 12/1973 | Friedman | ..................... 602/24 |
| 3,892,231 A * | 7/1975 | Tummillo | .................... 602/24 |
| 4,088,129 A | 5/1978 | DiGiulio | |
| 4,249,523 A | 2/1981 | Bidwell | |
| 4,495,943 A | 1/1985 | Kurtz et al. | |
| 5,346,463 A | 9/1994 | Devens | |
| 5,382,225 A | 1/1995 | Sutcliffe | |
| 5,401,235 A | 3/1995 | Devens | |
| 5,470,310 A * | 11/1995 | Sutcliffe | ..................... 602/24 |
| 5,483,757 A * | 1/1996 | Frykberg | ..................... 36/101 |
| 5,489,258 A | 2/1996 | Wohnsen et al. | |
| 6,094,844 A | 8/2000 | Potts | |
| 6,173,511 B1 | 1/2001 | Perrault | |
| 6,328,707 B1 | 12/2001 | Lampkins | |
| 2004/0244221 A1 | 12/2004 | Hall et al. | |

OTHER PUBLICATIONS

A web page showing an article from the Department of Mechanical Engineering at the University of Michigan entitled "Design Expo: Fall 2002" regarding the Dennis Browne Splint.

* cited by examiner

*Primary Examiner*—Loan Thanh
*Assistant Examiner*—Tarla R Patel
(74) *Attorney, Agent, or Firm*—Simmons Perrine Moyer Bergman PLC

(57) ABSTRACT

A system and method for comfortably restraining a child's feet undergoing the Ponseti method for treatment of clubfeet, using a foot and ankle abduction orthosis, where the improvement includes a shoe with a single piece sole and quick release slot with an adjustable hinged heel support member, as well as having a soft pliable area around the feet and ankle support with lateral support bands to limit foot plantar flexion.

17 Claims, 17 Drawing Sheets

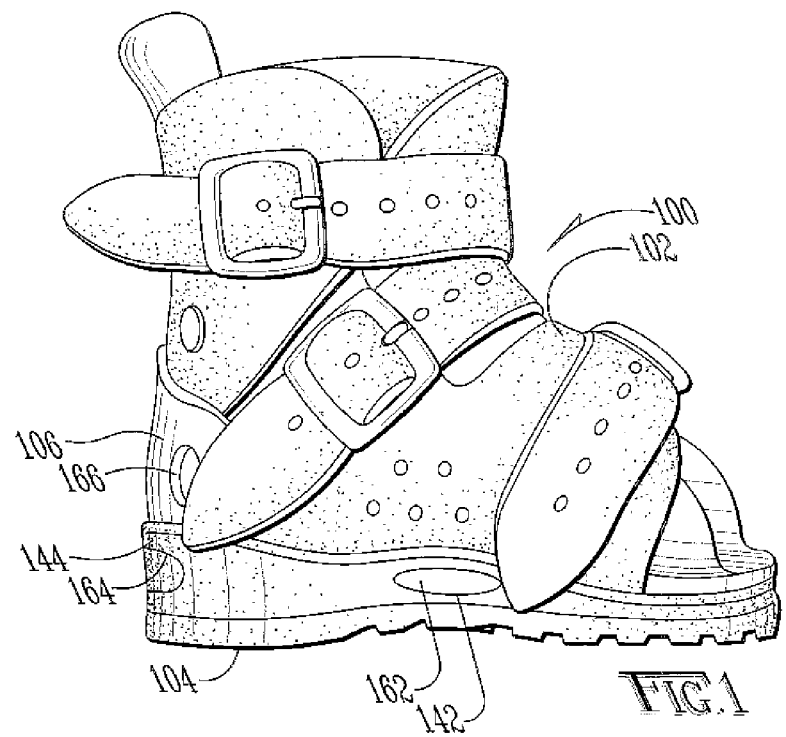
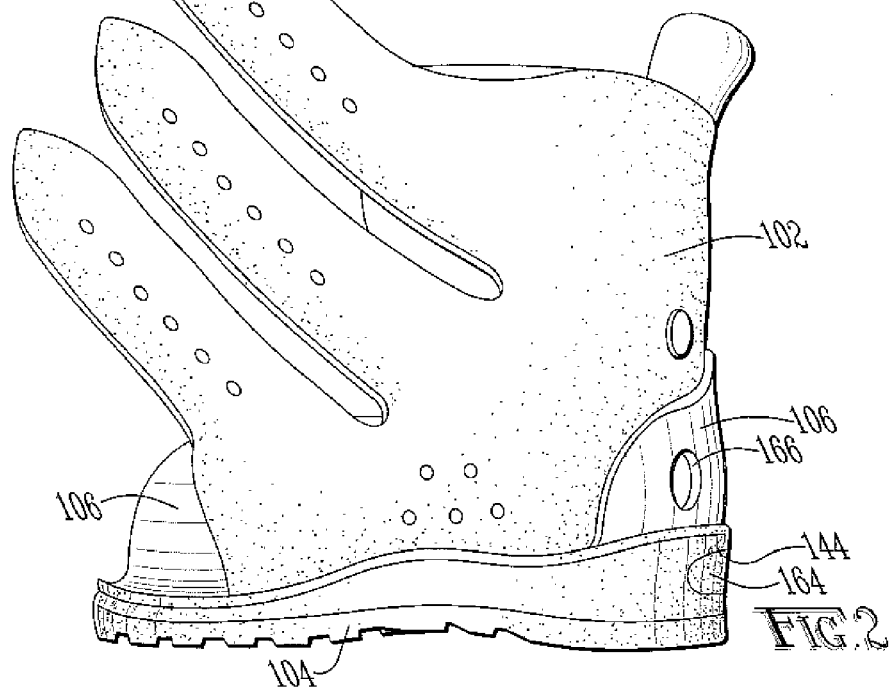

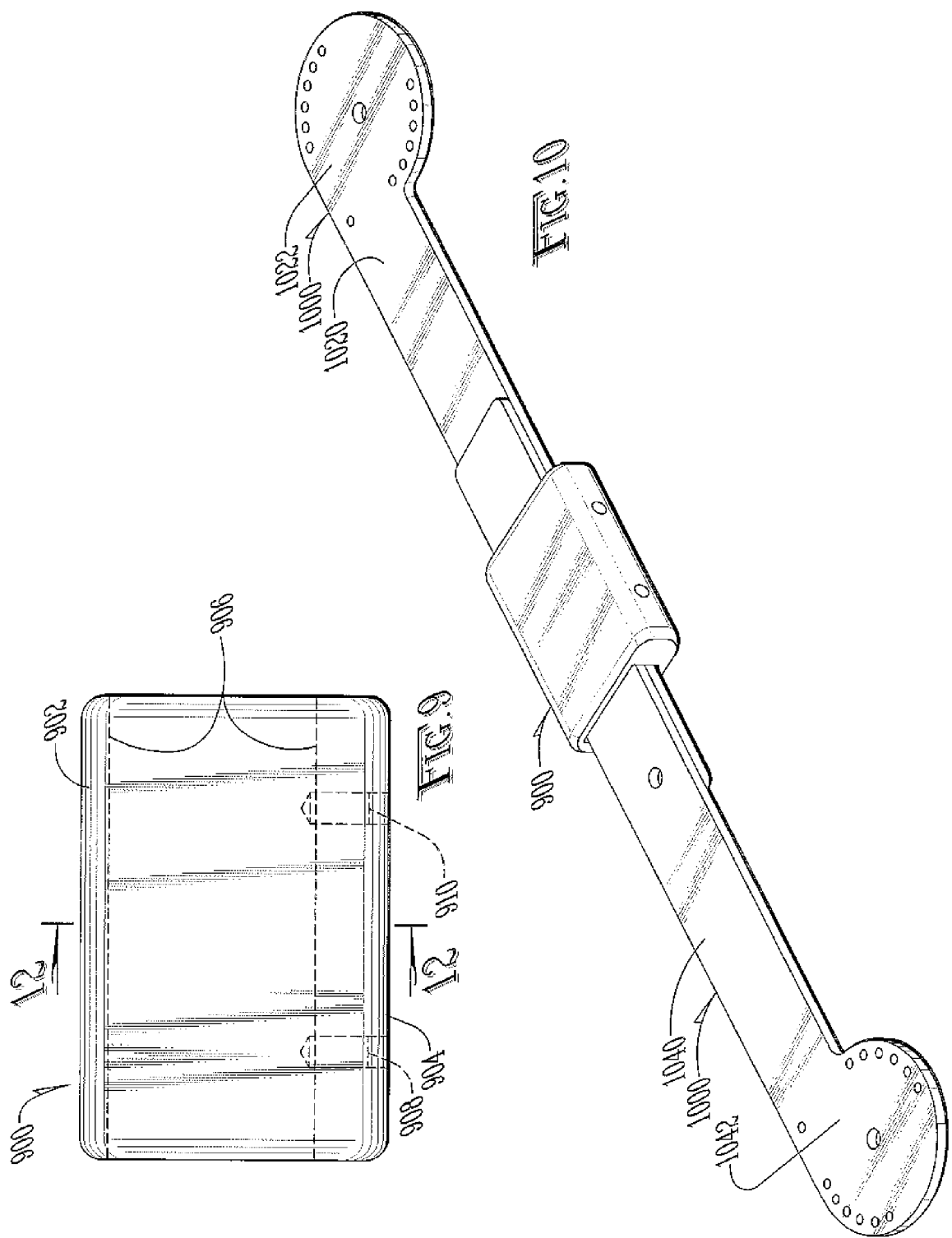

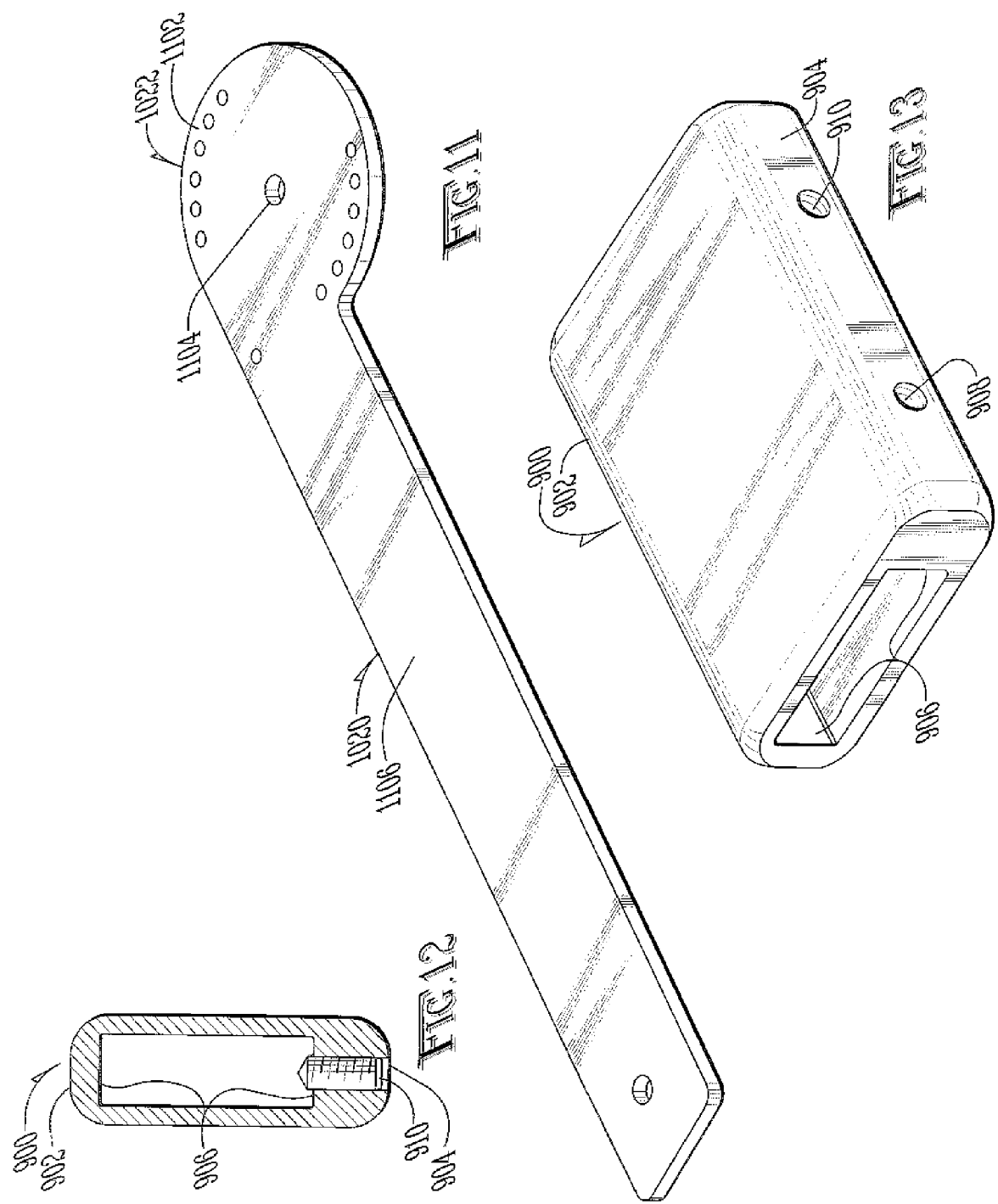

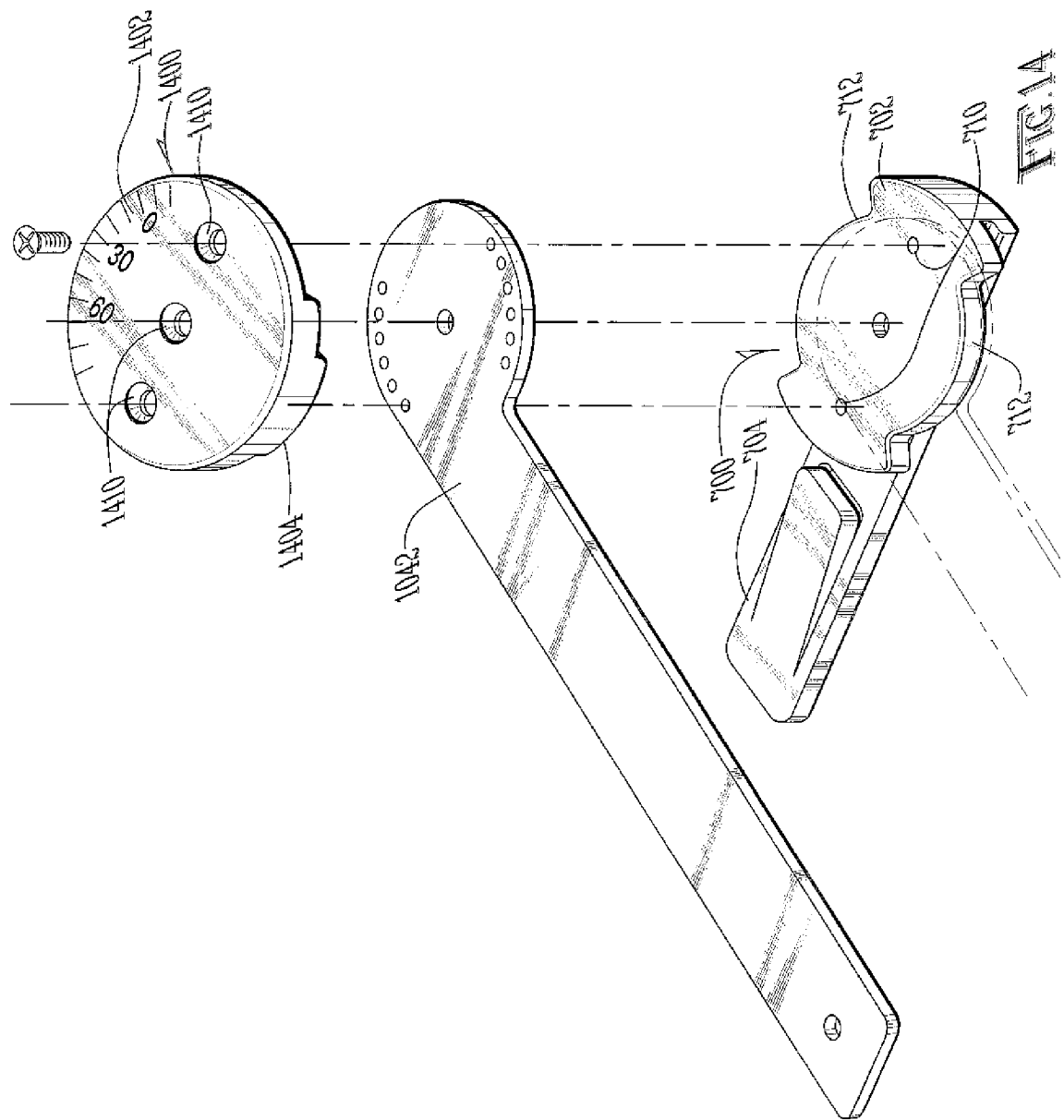

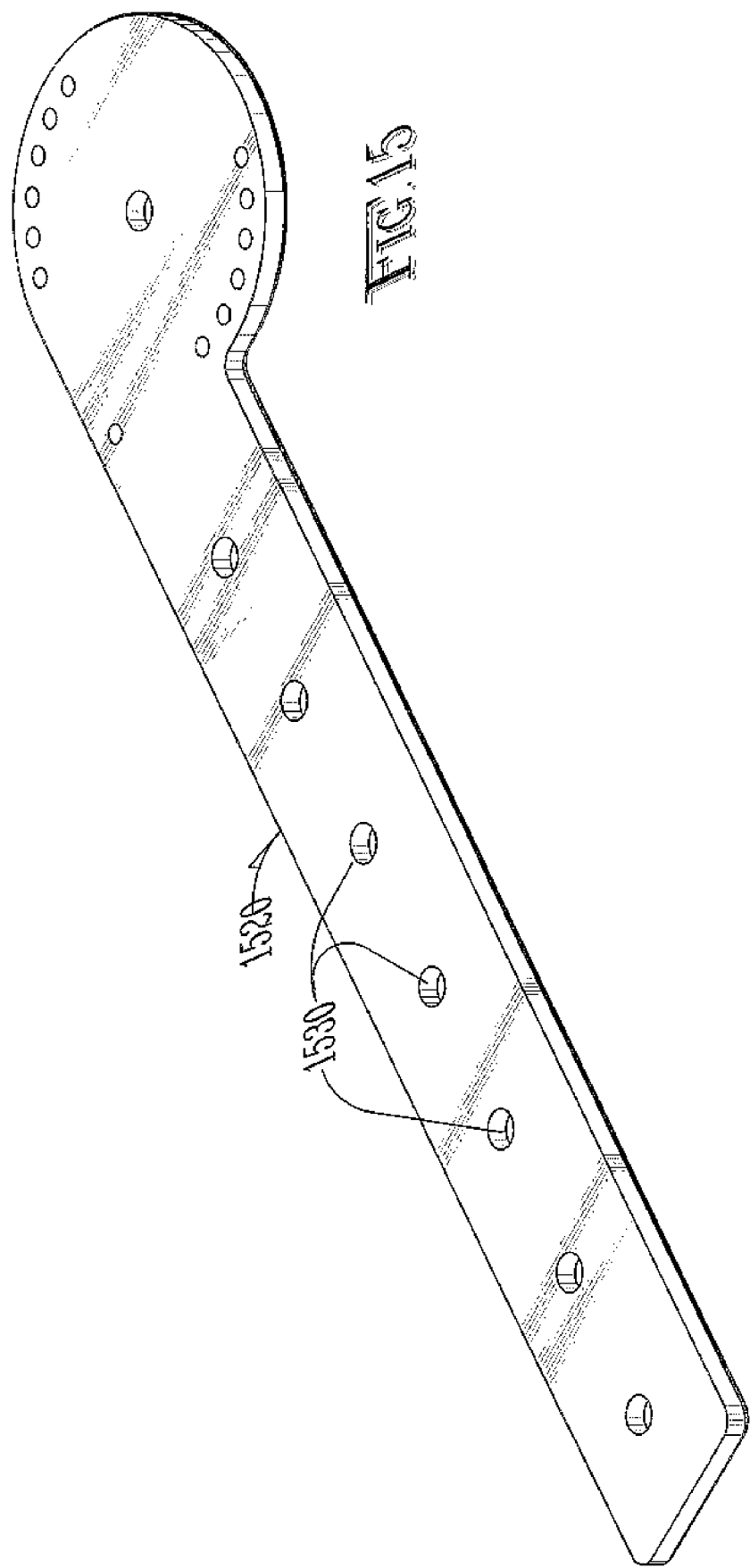

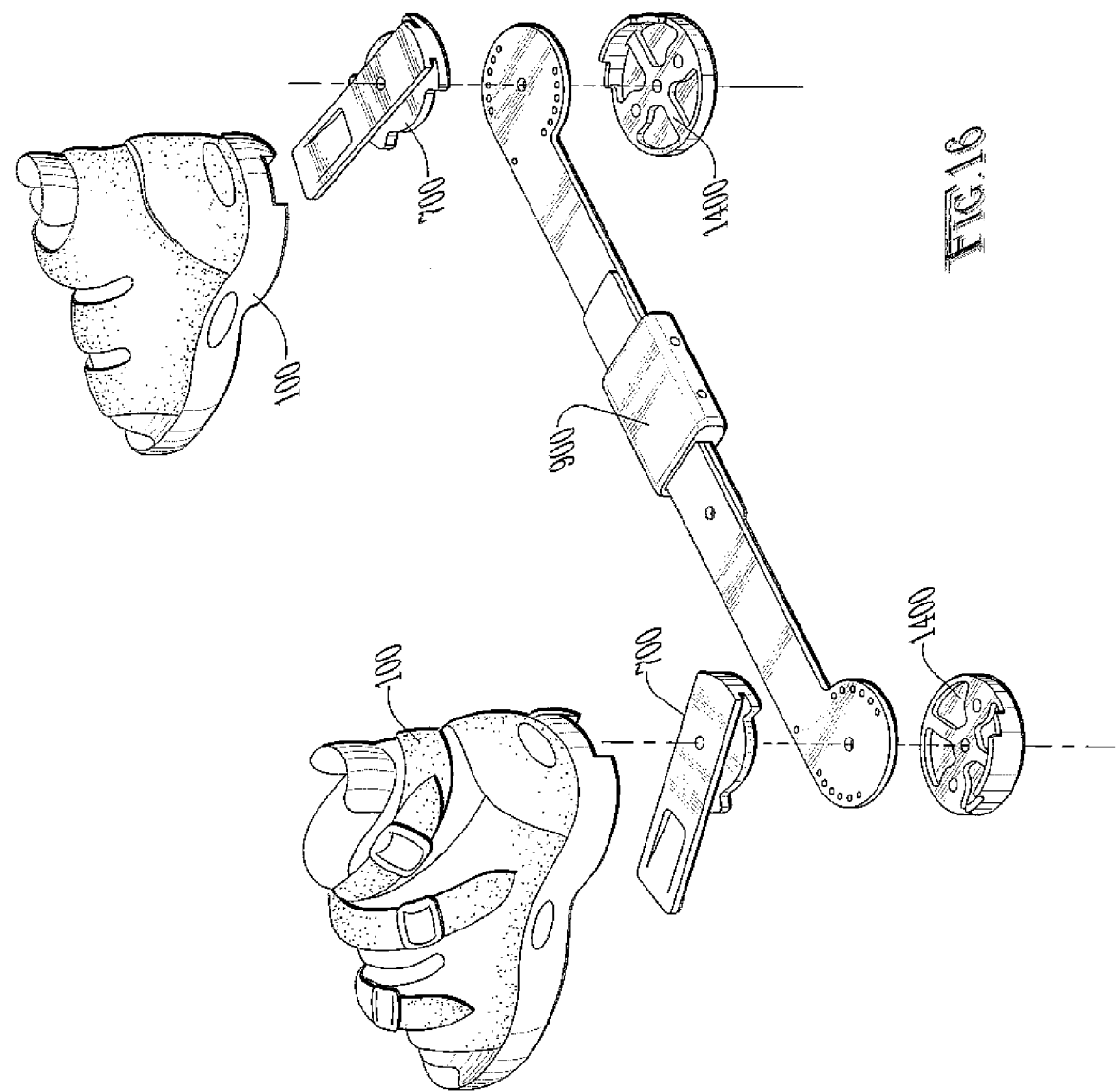

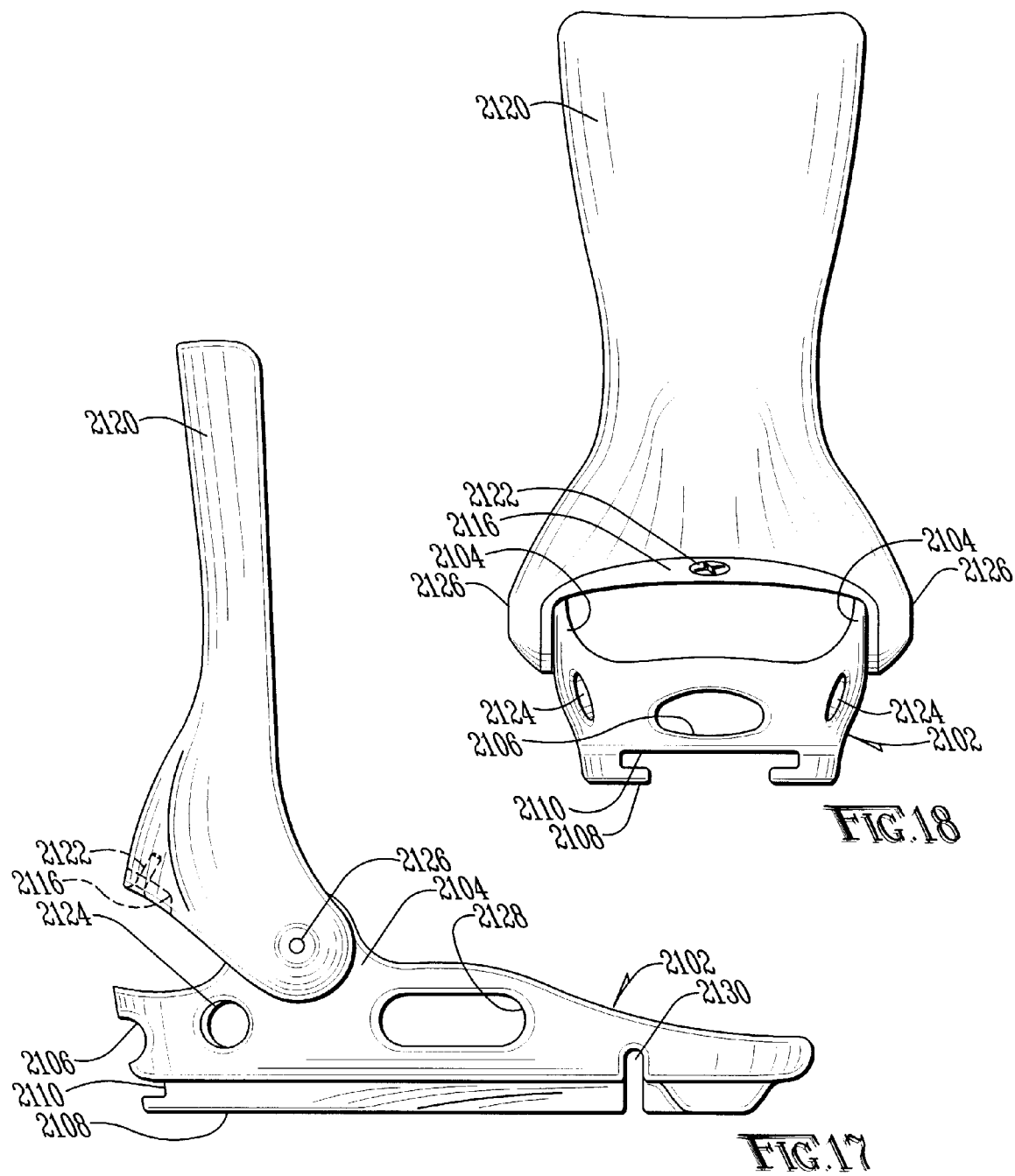

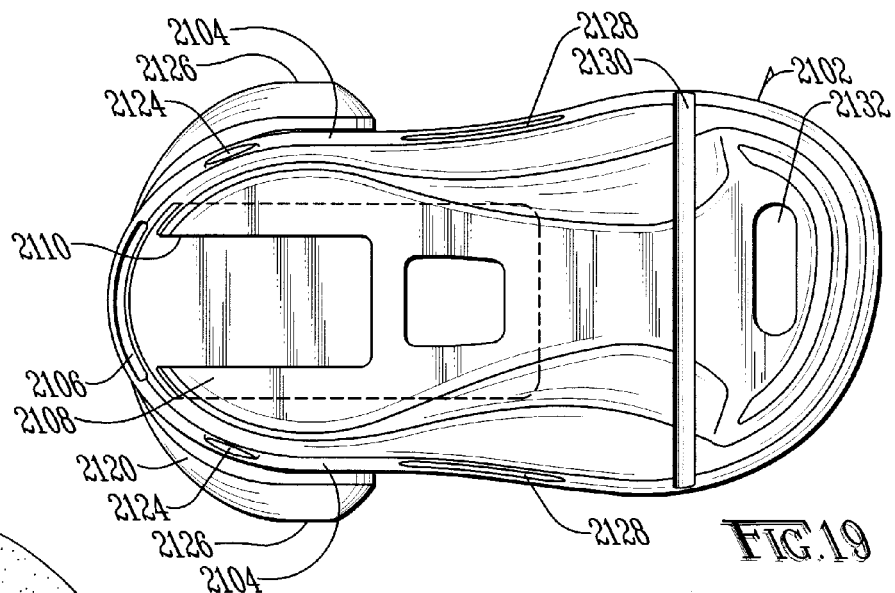
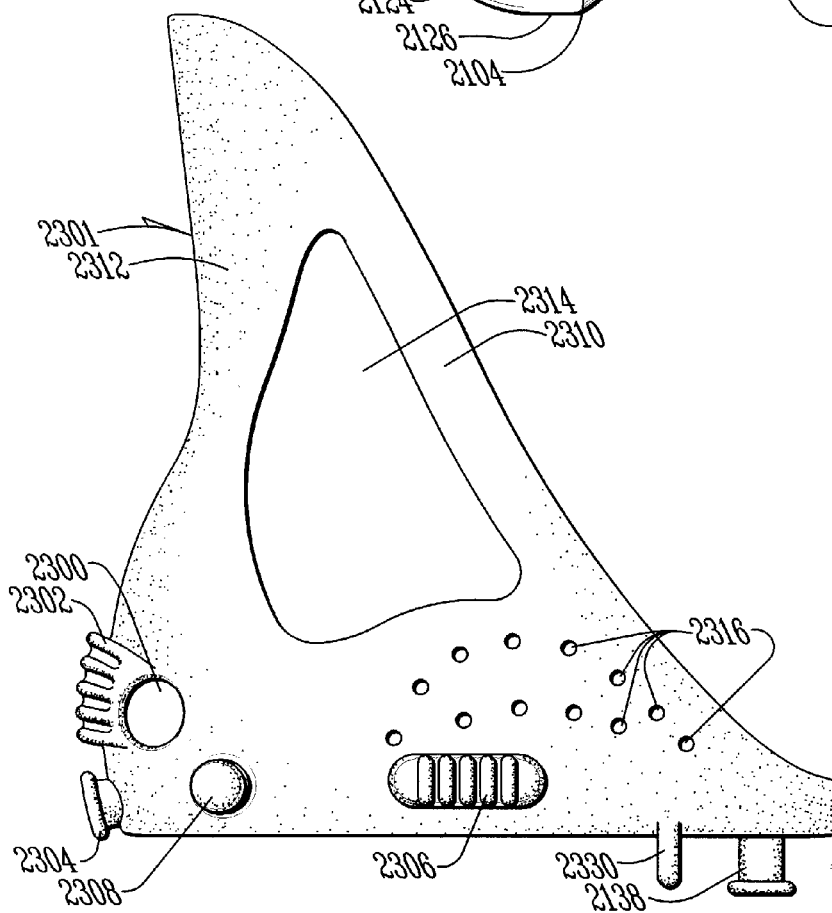

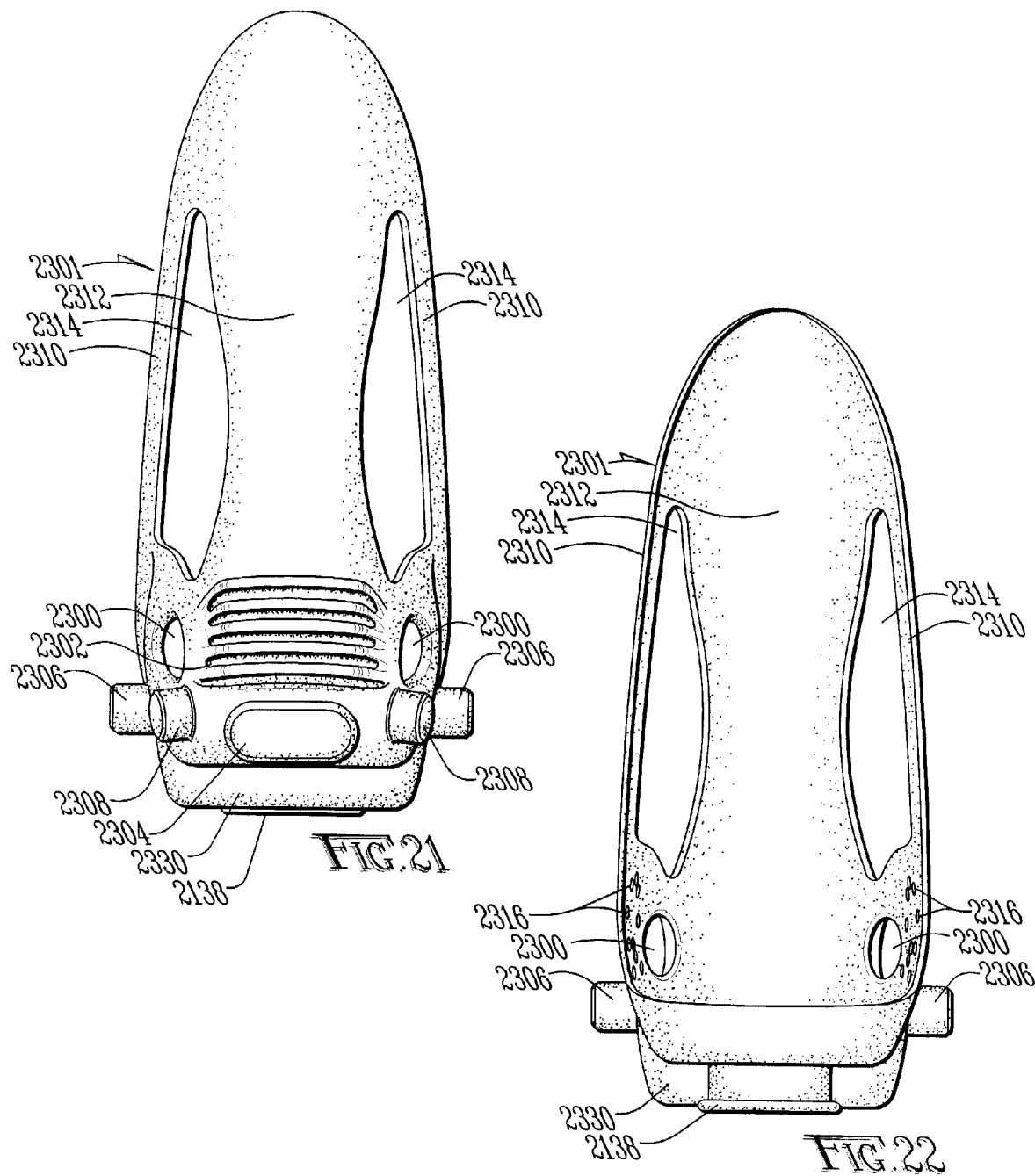

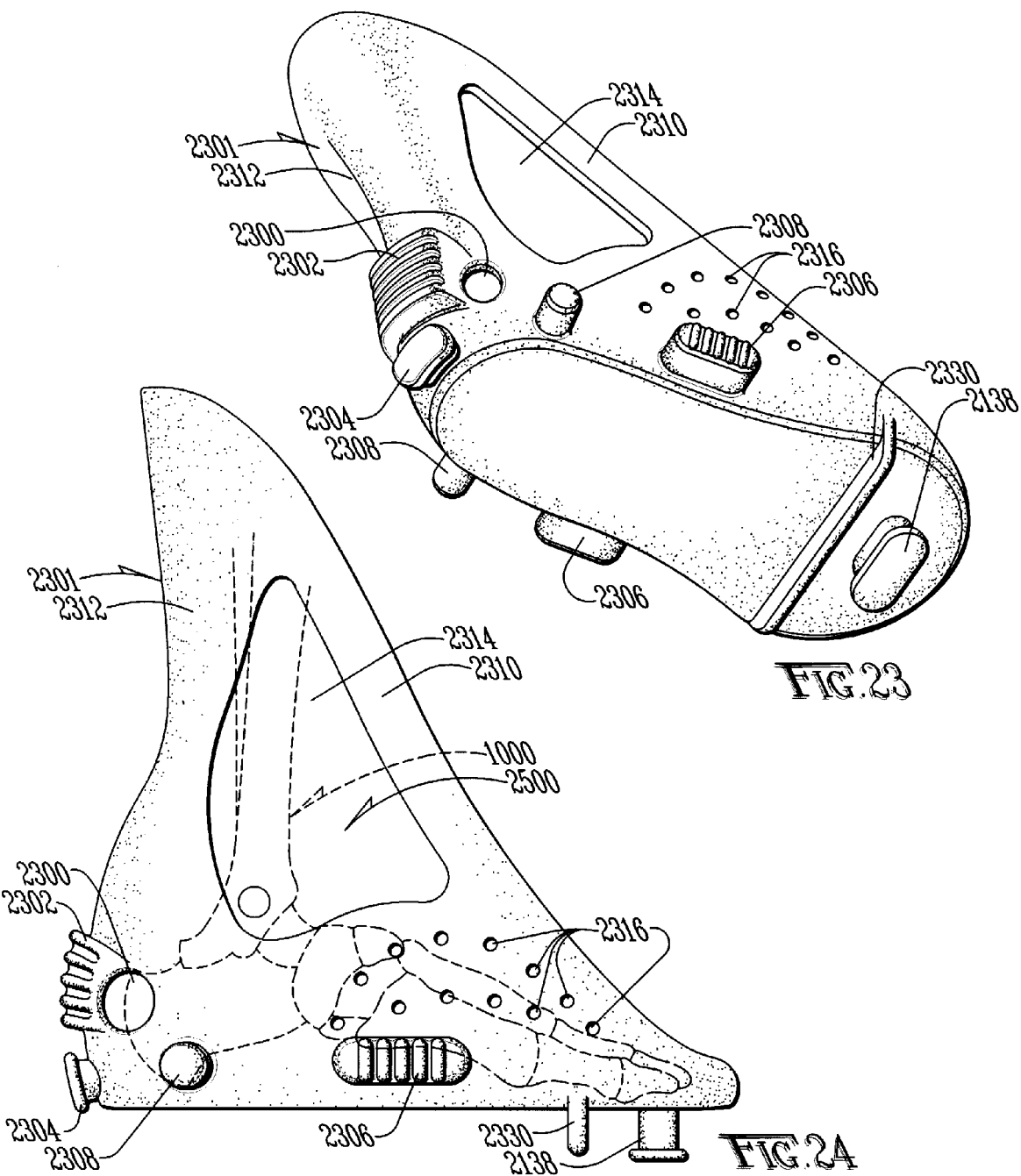

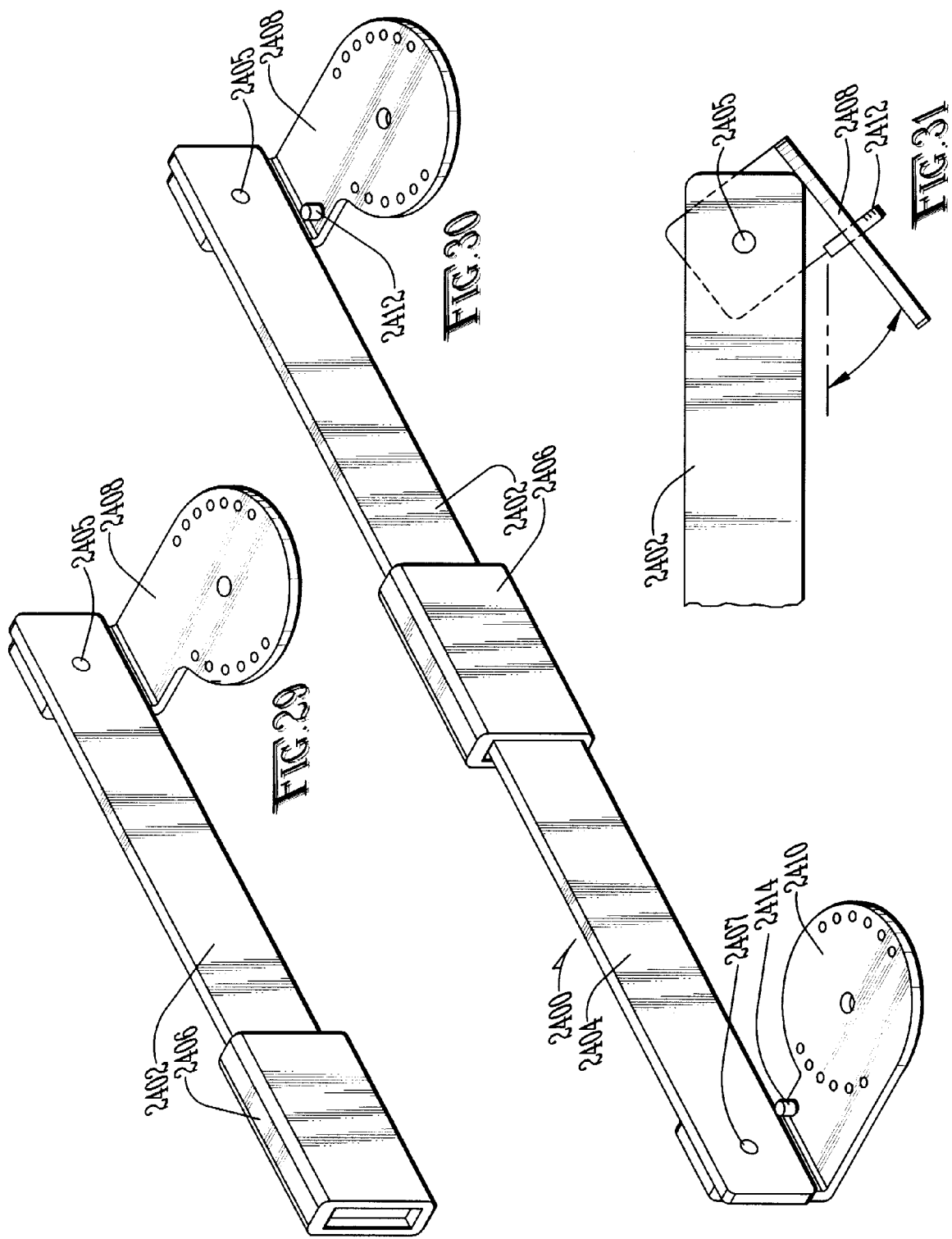

SYSTEM AND METHOD FOR CORRECTING CLUBFOOT PROBLEMS IN CHILDREN

CROSS-REFERENCE TO RELATED APPLICATIONS

This application is a continuation-in-part of co-pending application Ser. No. 10/708,808, which was filed on Mar. 26, 2004, for "System and method for correcting club foot problems in children" by the same inventor, and also claims the benefit of provisional application No. 60/767,049 filed on Feb. 28, 2006 for "articulated ankle foot orthotic" by the same inventor, which applications and patents are incorporated herein in their entirety by this reference.

FIELD OF THE INVENTION

The present invention generally relates to treatment of clubfoot deformity in infants and very young children, and more particularly relates to shoes and brace systems for aligning feet, devised to replace the Denis Browne splint. A Foot and Ankle Abduction Orthosis has been devised to prevent relapses of corrected clubfeet by firmly, yet gently and comfortably, holding the baby's feet in the corrected position. Improvements have been made to aid the patient's comfort and convenience, as well as improving mobility.

BACKGROUND OF THE INVENTION

For years, Dr. Ignacio Ponseti, a world-renowned expert in the treatment and management of clubfeet, has advocated use of a foot and ankle abduction orthosis (AFO) to prevent relapses of the deformity after the clubfoot is corrected. Such a device consists of a bar of about the length between the baby's shoulders with high top open-toed shoes attached at the end of the bar in about 60 degrees of outward rotation. The splint is worn full time for two to three months, and thereafter at night and naptime for 2 to 4 years. Corrective adjustments to the foot alignment are often necessary.

For many years, Dr. Ponseti used, with great success, the well-designed round-heeled high-top commercial shoes made by Penney's with soft leather. These are no longer available, and companies supplying much of the industry today don't produce adequate shoes attached to the bar. They often cause pressure sores and blisters on the baby's tender feet. Short and chubby clubfeet, even when well corrected, slip inside the shoe and even out of it, causing sores, loss of correction, great discomfort to the child and anguish to the parents.

Another problem is that it is often difficult to properly put the shoes on the patient's feet. In some instances, parents try to put the child's feet in the shoes while the shoes remain attached to the Denis Browne splint. It is not only difficult for the parent, but uncomfortable for the child. Others have proposed shoes which have a simple latch mechanism which is attached to the sole of the shoe. Such a combination allows the parent to put the shoes on the child first and then latch the shoes to the Denis Browne splint. These mechanisms attached to the bottom of the shoe are not only unsightly, but they are clumsy for the child to handle.

Consequently, there is an urgent need for improved methods and systems that will prevent relapses and sores while allowing free knee and ankle motion necessary to develop leg muscle strength.

SUMMARY OF THE INVENTION

It is an object of the present invention to provide a system and method for retaining a child's foot in an efficient manner.

It is a feature of the present invention to utilize a shoe with a sole and heel combination having an integrated attachment mechanism for connecting to a foot and ankle abduction splint (or orthosis) (AFO).

It is an advantage of the present invention to permit a child to wear a non-conspicuous and a normal use interference-free shoe which is readily attachable to an AFO splint.

It is another feature of the present invention to include a shoe having an opening at the heel which permits viewing of both sides of the heel when disposed in the shoe.

It is an advantage of the present invention to achieve improved efficiency in fully inserting a child's foot into a shoe.

It is yet another feature of the present invention to include a relatively inflexible sole section, a pliable interior foot cradling segment, and a relatively flexible shoe upper section.

It is an advantage of the present invention to provide comfort and firm support to a patient's feet.

It is still another feature of the present invention to include a two-piece flexible sole where each piece is relatively inflexible, a pliable interior foot cradling segment which has diagonal support bands extending from an elevated rear or heel position to a lower position nearer the toes, and a relatively flexible shoe upper section, in combination with a pivoting rigid and adjustable heel support section which pivots with respect to the sole.

Further advantages of the present invention include increased flexibility of the sole to aid in walking, increased support of the toes to prevent unwanted dropping of the toes with respect to the heel, and increased and adjustable upper heel support.

Yet another feature of the present invention is to include pivot points at each of the rigid bar or rigid bar halves.

It is yet another advantage to permit limited rotational movement of the shoe with respect to the bar in a predetermined manner.

The present invention is an apparatus and method for holding a child's feet in a predetermined therapeutic arrangement where the apparatus and method are designed to satisfy the aforementioned needs, provide the previously stated objects, include the above-listed features, and achieve the already articulated advantages. The present invention is carried out in a "discomfort-less" manner in a sense that much of the patient discomfort often associated with wearing, donning, and securing to an AFO splint, a pair of shoes, has been greatly reduced. Additionally, the invention is carried out in foot drop-less manner in the sense that the amount of foot drop is limited by the adjustable screw and the support bands.

Accordingly, the present invention is a system and method including a shoe having a sole and heel with an integral mating mechanism for mating with an AFO splint, a comfortable pliable inner foot cradle and a comfortable shoe upper for ankle support and further includes a pivoting shoe/bar connection and a pivoting heel support and sole connection.

BRIEF DESCRIPTION OF THE DRAWINGS

The invention may be more fully understood by reading the following description of the preferred embodiments of the invention, in conjunction with the appended drawings wherein:

FIG. 1 is a side view of a shoe of the present invention

FIG. 2 is a side to rear view of the shoe of FIG. 1 with the straps elevated for display purposes.

FIG. 9 is a top view of a central joining piece of the splint of FIG. 10, where the dashed lines refer to the edges of the elongated portions of the splint halves of FIG. 11.

FIG. 10 is a perspective view of a splint of the present invention, including a central joining piece of FIG. 9 and opposing splint halves of FIG. 11.

FIG. 11 is a perspective view of one of the opposing splint halves of the present invention.

FIG. 12 is a cross-sectional view of the central joining piece of FIG. 9 taken on line 12-12.

FIG. 13 is a perspective view of the central joining piece of FIG. 13.

FIG. 14 is an exploded view of the angular adjustment mechanism of the present invention.

FIG. 15 is a drilled horizontal cross piece for a splint of the present invention.

FIG. 16 is an exploded view of the foot wear, angular adjustment/quick release member and adjustable splint assembly of the present invention.

FIG. 17 is a side view of an AFO of the present invention.

FIG. 18 is a back side view of the AFO of FIG. 17.

FIG. 19 is a bottom view of an AFO of FIG. 17 which shows a gap for permitting flexing when walking.

FIG. 20 is a side view of the pliable foot cradling insert.

FIG. 21 is a back side view of the insert of FIG. 20.

FIG. 22 is a front view of the insert of FIG. 20.

FIG. 23 is a perspective view of the insert of FIG. 20.

FIG. 24 is a side view of the insert of FIG. 20 where the intermittent lines represent bones of a foot when located inside of the insert.

FIG. 29 is a view of a portion of a rigid bar and shoe attachment plate, where the arrow shows the direction of relative movement of plate with respect to the rigid bar around pivot point.

FIG. 30 is a view of both sides of a rigid bar as shown in FIG. 29.

FIG. 31 is a close-up view of the joint at pivot point.

DETAILED DESCRIPTION

Figure 3:
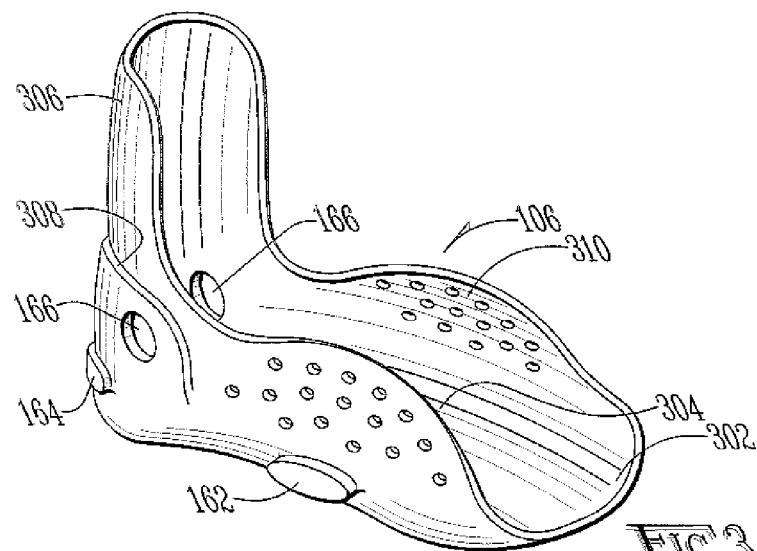
FIG. 3 is a perspective view of the in-foot cradle of FIG. 1.

Now referring to the drawings wherein like numerals refer to like matter throughout, and more specifically referring to FIG. 1 there is shown an article of footwear 100, of the present invention. Footwear 100 is shown having an upper 102 which could be any type of material, including leather, fabric, vinyl or other material suitable for a shoe or sandal. Footwear 100 further includes a sole 104, which is preferably a single molded piece of plastic material, such as a flexible polymer. Other material suitable for shoe or sandal soles could be used as well. Also shown is insole 106, which is disposed above upper 102 and generally within upper 102. Preferably, insole 106 is a single piece of molded polyurethane or rubber-like material. Preferably, insole 106 is pliable enough so as to permit it to conform to the shape of a child's foot when inserted therein and secured thereon by upper 102.

Insole 106 is secured to sole 104 by glue and may be supplemented, if necessary, providing an insole side protuberance 162 to extend through a sole side hole 142 in sole 104. Similarly, insole heel protuberance 164 extends through sole heel hole 144 and thereby holds insole 106 stable with respect to sole 104. Insole 106 is also shown having an insole heel right viewing hole 166, which is located near the heel of the insole 106, so that it can readily be seen that a child's foot is in contact with the insole 106. In a preferred embodiment, the insole heel right viewing hole 166 is a pair of holes on opposite sides of the heel or is a single hole which spans to both sides of the heel. In either embodiment, it would be possible to view the placement of the child's foot with respect to the insole 106 from a vantage point on either side of the heel.

Now referring to FIG. 2, there is shown an opposite side of footwear 100 of FIG. 1.

Now referring to FIG. 3, there is shown a perspective view of the insole 106 of FIG. 1 when it is separated from footwear 100. Insole 106 is shown having an insole toe end 302 and an insole sole foot side 304. Preferably, insole sole foot side 304 is generally a flat surface without substantial contours to fit to an arch of a foot. Insole 106 includes an insole heel and ankle support 306 with an insole strap support 308 which keeps an ankle support strap from slipping downward. Insole 106 further includes insole side wall 310 on opposing sides of insole sole foot side 304. In a preferred embodiment, insole sole foot side 304, insole side wall 310 and insole heel and ankle support 306 all are portions of a single molded piece of urethane, pliable rubber-like material or flexible polymer material.

Figure 4:
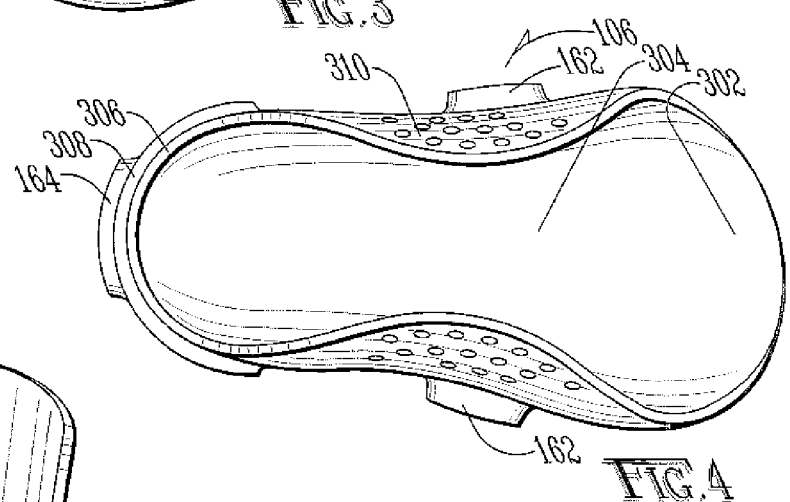
FIG. 4 is a front view of the foot cradle of FIG. 3.
Figure 5:
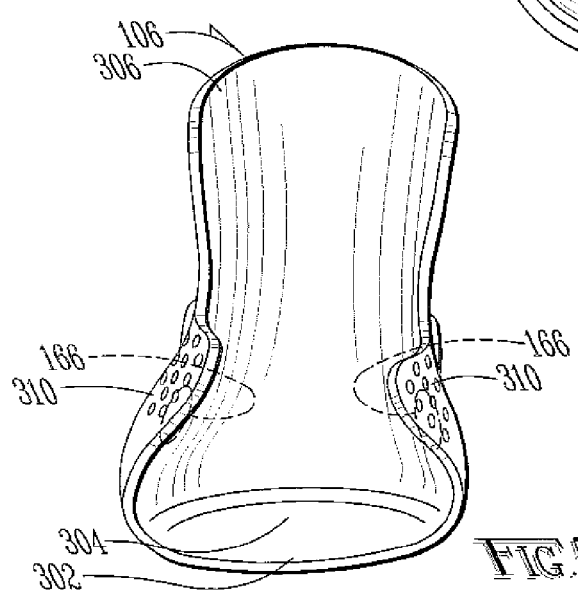
FIG. 5 is a top view of the foot cradle of FIG. 4.

Now referring to FIGS. 4 and 5 top view, there are shown front and top views, respectively of the insole 106 of FIGS. 1, 2 and 3.

Figure 6:
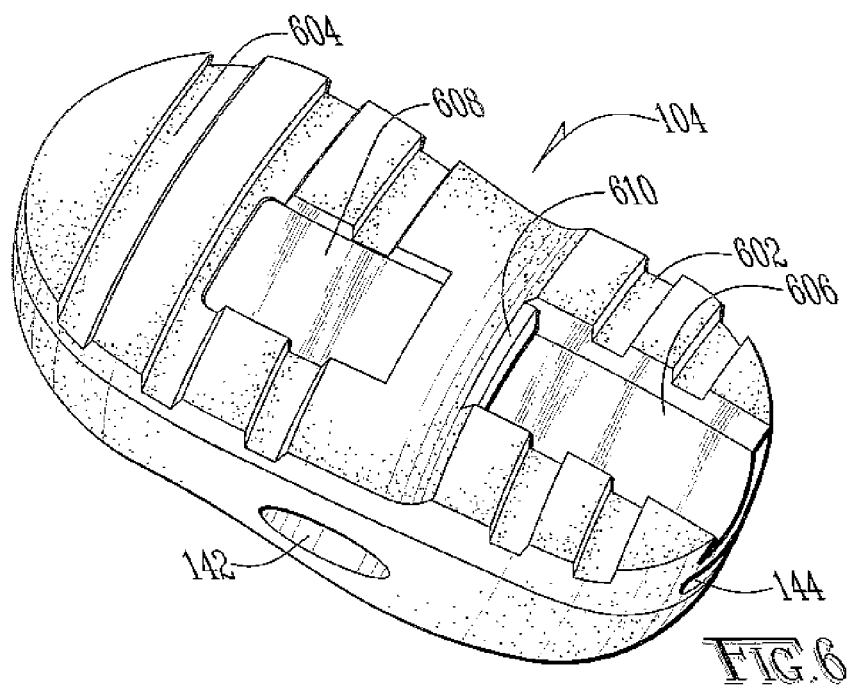
FIG. 6 is a bottom view of the sole portion of the shoe of FIG. 1.

Now referring to FIG. 6, there is shown a perspective view of the bottom of sole 104 of the footwear 100 of FIG. 1. Sole heel 602 is shown disposed at an opposite end of sole 104 from sole toe end 604. Sole heel 602 has a sole attachment receiving groove 606 therein, which is separated from quick release push button receiving void 608 by quick release button barrier 610. Preferably, all of these features, sole heel 602, sole toe end 604, sole attachment receiving groove 606, quick release push button receiving void 608 and quick release button barrier 610, are integrally formed in a single piece of durable plastic or other material suitable for a rigid shoe sole. This material may need to be more rigid than a typical shoe sole material because of the need for increased lateral forces owing to the use of the splint between the shoes.

Figure 7:
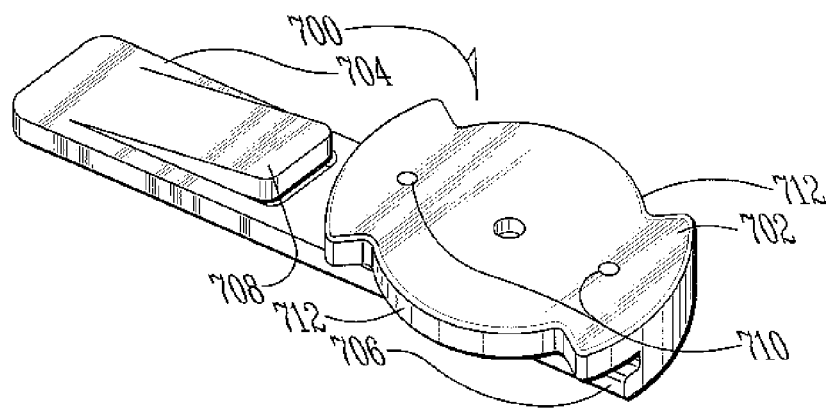
FIG. 7 is a bottom view of the clip mechanism of the present invention.
Figure 8:
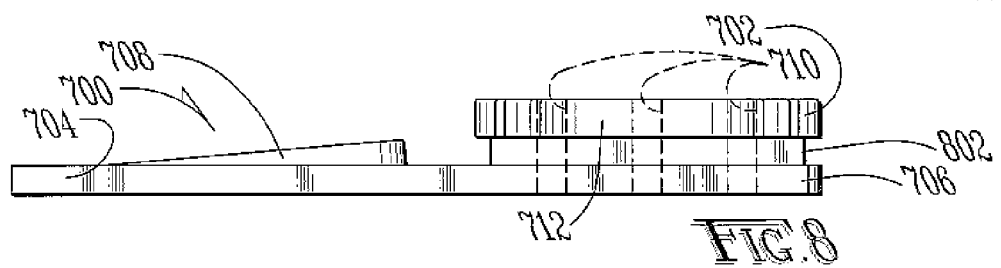
FIG. 8 is a side view of the clip mechanism of FIG. 7 in combination with an adjustment end of the bar of FIGS. 11 and 12.

Now referring to FIG. 7, there is shown an angular adjustment/quick release member 700, which is configured to be inserted into sole attachment receiving groove 606 and quick release push button receiving void 608 of FIG. 6, by first inserting quick release front end 704 into sole attachment receiving groove 606 and sliding in further until quick release button 708 snaps into a locked position in quick release push button receiving void 608. Quick release button 708 is preferably biased outward by a spring-like structure or arrangement. Angular adjustment/quick release member 700 includes angular adjustment base 702, which is coupled to quick release back end 706 by angular adjustment/quick release riser 802 (FIG. 8). Angular adjustment base 702 has a plurality of angular adjustment fixing screw mating holes 710 therein. Angular adjustment base 702 further has a pair of angular adjustment grooves 712 therein for receiving portions of groove penetrating portion 1402 (FIG. 14).

Now referring to FIG. 8, there is shown a side view of the angular adjustment/quick release member 700 of FIG. 7.

Now referring to FIG. 9, there is a cross-section view of a shoe separation setting device 900, also shown in FIGS. 10, 12 and 13. The dashed lines show the shoe separation bar-receiving cavity edges 906. Shoe separation setting device 900 has a shoe separation setting device back side 902 and a shoe separation setting device front side 904, as well as a first set screw 908 and a second set screw 910. Preferably, shoe separation setting device 900 is made of a strong and rigid plastic material. First set screw 908 and second set screw 910 are shown extending through the shoe separation setting device front side 904 of shoe separation setting device 900. The purpose of first set screw 908 and second set screw 910 is to function as a set screw fixing the location of adjustable splint right rigid bar 1020 and adjustable splint left rigid bar 1040 (FIG. 10) at a set point. The therapeutic benefits of the Ponseti Method require that the separation of the feet be adjustable to differing fixed amounts during the treatment. The first set screw 908 and the second set screw 910 permit this adjustment. These set screws function similarly to the set screws found in the AFO or Markell Denis Browne Splint discussed above.

Now referring to FIG. 10, there is shown an adjustable splint assembly 1000 which includes a shoe separation setting device 900, an adjustable splint right rigid bar 1020, having an adjustable splint right angular adjustment end 1022 and an adjustable splint left rigid bar 1040 having an adjustable splint left angular adjustment end 1042. Preferably adjustable splint right rigid bar 1020 and adjustable splint left rigid bar 1040 are rigid and strong metal bars; however, other suitable materials could be used as well.

Now referring to FIG. 11, there is shown a close-up view of the adjustable splint right rigid bar 1020 of FIG. 10. Adjustable splint right rigid bar 1020 has a plurality of adjustable splint right angular adjustment end adjustment screw holes 1102 and an adjustable splint right angular adjustment end center screw hole 1104 in the adjustable splint right angular adjustment end 1022. Adjustable splint right rigid bar 1020 has a right rigid bar shank 1106, which extends into the shoe separation setting device 900 of FIG. 10. Adjustable splint right rigid bar 1020 is designed to be used with the shoe separation setting device 900.

Now referring to FIG. 12, there is shown a cross-sectional view of the shoe separation setting device 900 of FIGS. 9 and 13.

Now referring to FIG. 13, there is shown a perspective view of the shoe separation setting device 900 of FIGS. 9, 10 and 12.

Now referring to FIG. 14, there is shown an exploded view of a complete assembly of the present invention in the area around the angular adjustment section of one end of the adjustable splint assembly 1000. There is shown the angular adjustment/quick release member 700 with its angular adjustment fixing screw holes 710. Adjustable splint left angular adjustment end 1042 is then disposed on angular adjustment base 702, so that it fits inside the angular adjustment grooves 712 and that the center hole in adjustable splint left angular adjustment end 1042 aligns with the center of the angular adjustment fixing screw holes 710. Then, the adjustable splint left angular adjustment end 1042 is held in place with respect to the angular adjustment/quick release member 700 when angular adjustment guide cap 1400 is placed over the adjustable splint left angular adjustment end 1042 and the groove penetrating portion 1402 fits into one of the angular adjustment grooves 712. The rigid bar clearance riser 1404 gives space for the adjustable splint left angular adjustment end 1042 to rest on the angular adjustment base 702. The center of the angular adjustment screw holes 1410 is aligned with the center of the angular adjustment fixing screw holes 710 and the center hole in adjustable splint left angular adjustment end 1042, and a screw is inserted therein. With this arrangement, the quick release front end 704 and the adjustable splint left rigid bar 1040 are able to be moved to and locked into a series of discrete angular adjustments.

Now referring to FIG. 15, there is shown a bolt through rigid bar 1520 which is similar in overall function to adjustable splint right rigid bar 1020 except that it is designed to have a bolt extend through the plurality of bolt through rigid bar bolt receiving holes 1530 therein. The bolt or bolts could perform the same function as the shoe separation setting device 900, namely, fixing the overall combined length of the two bars and, therefore, the separation distance between the patient's feet.

Now referring to FIG. 16, there is shown an exploded view of the present invention with two shoes coupled together.

In operation, the present invention can be used to carry out the Ponseti method of clubfoot treatment as follows:

Adjustable splint right rigid bar 1020 and adjustable splint left rigid bar adjustable splint left rigid bar 1040 are coupled together using a bolt or shoe separation setting device 900. The angular adjustment mechanisms on each end of the adjustable splint assembly 1000 are assembled as described with respect to FIG. 14. The angle is set by inserting a second screw through one of the adjustable splint right angular adjustment end adjustment screw holes 1102. The footwear 100 is attached to the angular adjustment/quick release member 700 by insertion of the quick release front end 704 into the sole attachment receiving groove 606 and quick release push button receiving void 608 until the quick release button 708 snaps into place beyond the quick release button barrier 610. At this point, the patient's feet can be placed in the footwear 100 and secured. Proper placement of the feet in the footwear 100 can be assured by viewing through the insole heel right viewing hole 166.

In an alternate approach, the footwear 100 can be secured to the patient's feet and then the angular adjustment/quick release member 700 is coupled to the footwear 100.

Now referring to FIG. 17, there is shown an embodiment with several additional features beyond the embodiment shown in FIGS. 1-16. There is shown an ankle foot orthosis shoe sole 2102 which could be a single piece of thermal molded plastic, ABS, urethane or a suitable substitute. Ankle foot orthosis shoe sole 2102 may be in two parts where the toe section is detached or merely connected by a small connection section which permits flexing to occur between the two parts. This embodiment shows a flexion control plate 2120 which is coupled to ankle foot orthos is shoe sole 2102 via a hinge screw 2126 in raised hinge portion 2104. Flexion control plate 2120 pivots with respect to ankle foot orthosis shoe sole 2102 and the amount of permissible pivoting is regulated by the amount of insertion or protrusion of screw adjustment pad/foot 2116, which is adjustable, coupled to flexion control plate 2120 via flexion control plate angular adjustment screw 2122. If the flexion control plate angular adjustment screw 2122 is screwed out, then the screw adjustment pad/foot 2116 extends down further and will contact the rear shock matter 2302 (FIG. 20). Both Flexion control plate angular adjustment screw 2122 and screw adjustment pad/foot 2116 are shown in their least restrictive position; i.e., being fully seated into flexion control plate 2120. Ankle foot orthosis shoe sole 2102 is shown having numerous holes therein for receiving and retaining an insert. Rear button insertion hole 2106, side button insertion hole 2124, front side button insertion hole 2128 and sole flex permitting slot 2130 are shown.

The ankle foot orthosis shoe sole 2102 may have a sub sole heel raising matter 2108 to slightly raise the heel of the patient and for providing support for heel clip snap slot 2110, for receiving a heel clip similar to that shown in FIGS. 7 and 8.

Now referring to FIG. 18, there is shown a rear end view of the embodiment of FIG. 17.

Now referring to FIG. 19, there is shown a top view of the embodiment of FIG. 17 which shows a sole flex permitting slot 2130 and a bottom button insertion hole 2132. Sole flex permitting slot 2130 is shown as extending nearly across the entire bottom of ankle foot orthosis shoe sole 2102 except for a very narrow band which permits flexing and allows for the toe portion to remain attached. However, in another embodiment, the toe portion may be entirely separate and detached if the sole flex permitting slot 2130 extends entirely across the ankle foot orthosis shoe sole 2102 (i.e. the toe section is cut off from the remainder of the sole.) The purpose of bottom button insertion hole 2132 is to receive the toe insertion button to retain the pliable foot cradling insert 2301 to the toe section of the sole.

Now referring to FIG. 20, there is shown a pliable foot cradling insert 2301 which is similar in many respects to the insert of the embodiment of FIGS. 1-16; however, numerous differences exist. Pliable foot cradling insert 2301 includes a rear shock matter 2302 which extends between the ankle foot orthosis shoe sole 2102 and the flexion control plate 2120. The presence of rear shock matter 2302 between these members which have the ability to pivot with respect to each other provides for a limit on the angular orientation and also provides for a force dependent angular limitation. If the patient applies a more significant amount of relative force to increase the angular separation of the ankle foot orthosis shoe sole 2102 and the flexion control plate 2120, it will further compress the pliable material and allow for more angular separation. However, once that pressure is released, the rear shock matter 2302 will urge the pieces into a small angular separation. This permits a patient to perform foot plantar flexion if desired, but biases the foot into a non-dropped position when little or no force is applied. The amount of force that is required to move the pieces through various angles is determined by many factors, including the compressibility, the amount of and location of the rear shock matter 2302. Additionally, the angular orientation of the ankle foot orthosis shoe sole 2102 and the flexion control plate 2120 can be adjusted by adjusting the flexion control plate angular adjustment screw 2122 which will cause the screw adjustment pad/foot 2116 to protrude or retract and thereby adjust the angle of the flexion control plate 2120 with respect to the ankle foot orthosis shoe sole 2102. Pliable foot cradling insert 2301 also includes a pair of lateral foot drop limiting support bands 2310 which extend from an elevated position up the posterior Achilles support member 2312 to a forward position nearer the toes and the bottom of the pliable foot cradling insert 2301. Lateral foot drop limiting support bands 2310 provide resistance to foot plantar flexion or foot drop while providing for limited ability to force the foot to drop if desired. Preferably, lateral foot drop limiting support bands 2310 are made of the same type of material as the remainder of pliable foot cradling insert 2301, such as a silicon-based compound, polymer, thermal molded material, rubber, a strong elastic synthetic material, such as is made to provide improved qualities over natural rubber. Numerous pliable, compressible, and stretchable materials could be used. The width and thickness of lateral foot drop limiting support bands 2310, as well as the material of the bands, can be tailored to the particular needs of any one type of AFO; however, it is believed that a material which is not easily stretched a great amount is preferred.

A patient could cause a foot plantar flexion (foot drop) to occur, but it would be a temporary situation. Also, the patient could use the lateral foot drop limiting support bands 2310 and the rear shock matter 2302 to perform exercises to strengthen the muscles used to perform a foot plantar flexion. Pliable foot cradling insert 2301 further includes on each side ankle holes 2314 which are generally aligned with the patient's ankle joint where the ankle is near the bottom rear portion of the side ankle holes 2314. Additionally, side vent holes 2316 may be provided along the sides or at other locations as well. Pliable foot cradling insert 2301 has number buttons to mate with the numerous button holes in the ankle foot orthosis shoe sole 2102. Rear insertion button 2304, front side insertion button 2306 and side insertion button 2308, as well as bottom insertion button 2138, as well as pliable joint stop 2330, which may be some extra material in a gap in the ankle foot orthosis shoe sole 2102 so as to permit cushioned and limited flexing of the toe section relative to the heel section of ankle foot orthosis shoe sole 2102.

Now referring to FIG. 21, there is shown a rear end view of the pliable foot cradling insert 2301. It should be understood that the present invention need not include all of the features simultaneously. For example, one embodiment of the present invention might have the insert of FIG. 20 with the lateral foot drop limiting support bands 2310, but without the rear shock matter 2302. Another embodiment might include the insert with rear shock matter 2302, but without the lateral foot drop limiting support bands 2310.

Now referring to FIG. 22, there is shown a front end view of the pliable foot cradling insert 2301.

Now referring to FIG. 23, there is shown a perspective bottom view of the pliable foot cradling insert 2301.

Now referring to FIG. 24, there is shown a pliable foot cradling insert 2301 where the intermittent lines represent the bones of a patient's foot when the foot is properly placed inside the pliable foot cradling insert 2301 when it is placed in the ankle foot orthosis shoe sole 2102. The ankle joint 2500 is shown located in the lower back portion of side ankle holes 2314; however, other arrangements could be used as well. It is clear that the top of posterior Achilles support member 2312 is substantially higher up the patient's leg than the ankle joint.

Figure 25:
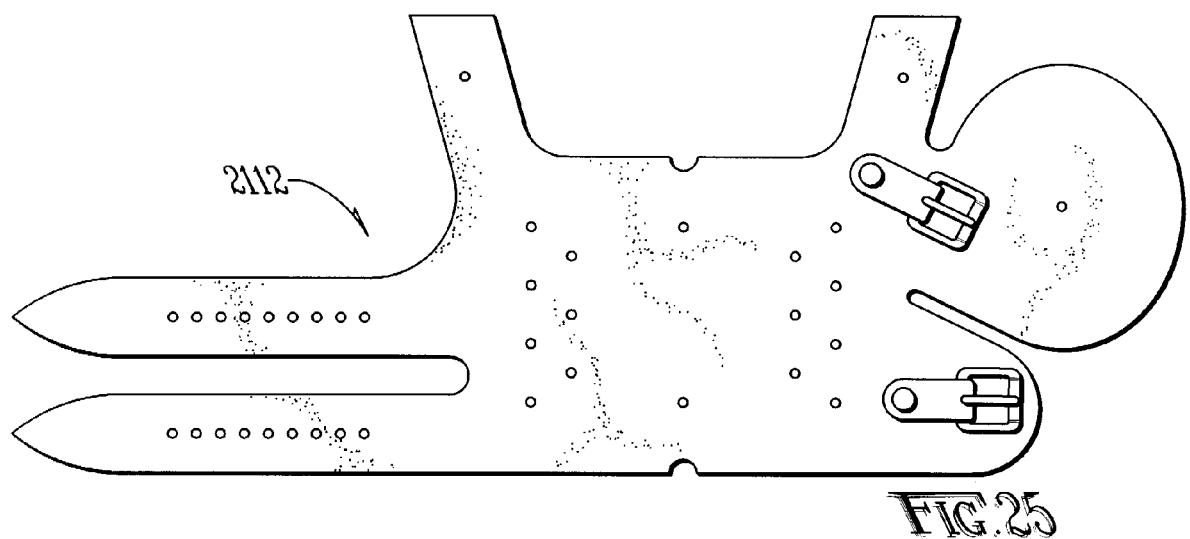
FIG. 25 is a view of a leather sandal body.
Figure 26:
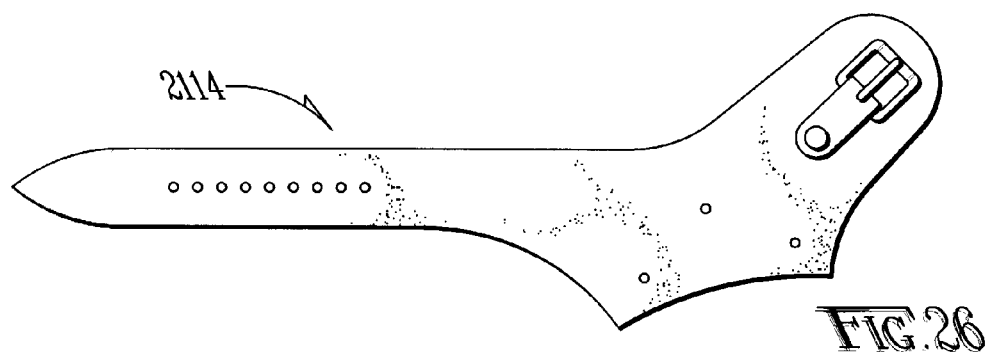
FIG. 26 is a view of a leather strap.

Now referring to FIGS. 25 and 26, there are shown flexible sandal body 2112 and the flexible sandal top strap 2114 respectively. These are preferably made from a soft brushed leather and stamped to have the proper shapes. Buckles and buckle pin receiving holes are also provided.

Figure 27:
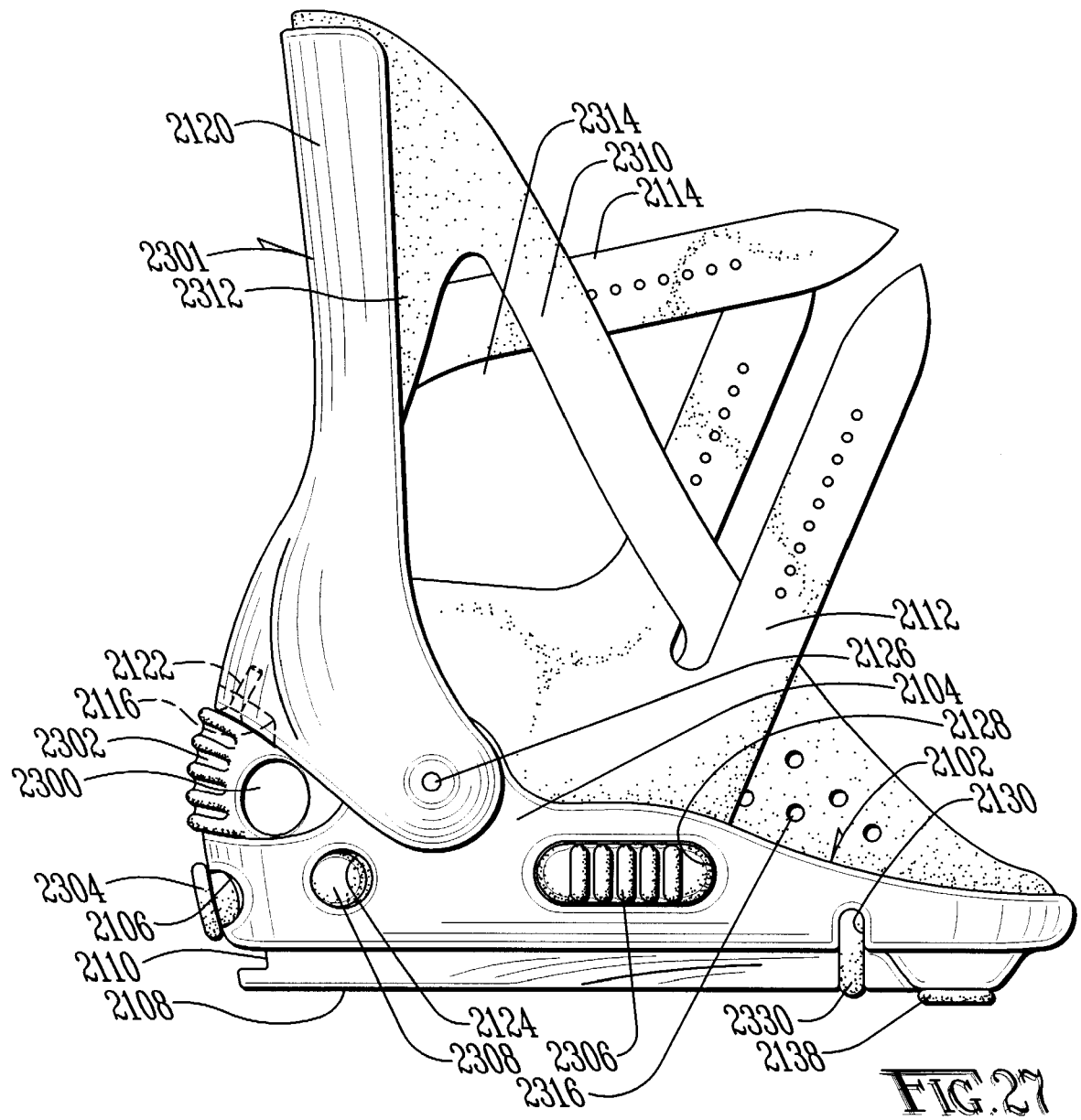
FIG. 27 is a side view of the entire shoe of the present invention.

Now referring to FIG. 27, there is shown a side view of the proper assembly of the ankle foot orthosis shoe sole 2102, flexion control plate 2120, pliable foot cradling insert 2301 flexible sandal body 2112 and the flexible sandal top strap 2114. The flexion control plate angular adjustment screw 2122 is shown screwed all of the way in. It is clear that if the flexion control plate angular adjustment screw 2122 were twisted and advanced outwardly, then the screw adjustment pad/foot 2116 would extend beyond and below its position as shown and, therefore, would cause the flexion control plate 2120 to be pushed forward with respect to the ankle foot orthosis shoe sole 2102 so as to reduce the angular separation between them. Heel viewing holes 2300 are clearly seen in the pliable foot cradling insert 2301 and disposed so that a parent or care provider can easily see that the patient's foot is fully inserted into the pliable foot cradling insert 2301 before it is finally strapped on and then attached to a rigid bar. Posterior Achilles support member 2312 bottom insertion button 2138 is shown extending through and beyond the bottom of the ankle foot orthosis shoe sole 2102. However, it may be preferred to have the bottom insertion button 2138 be much shorter and more nearly flush with the bottom of the ankle foot orthosis shoe sole 2102.

Figure 28:
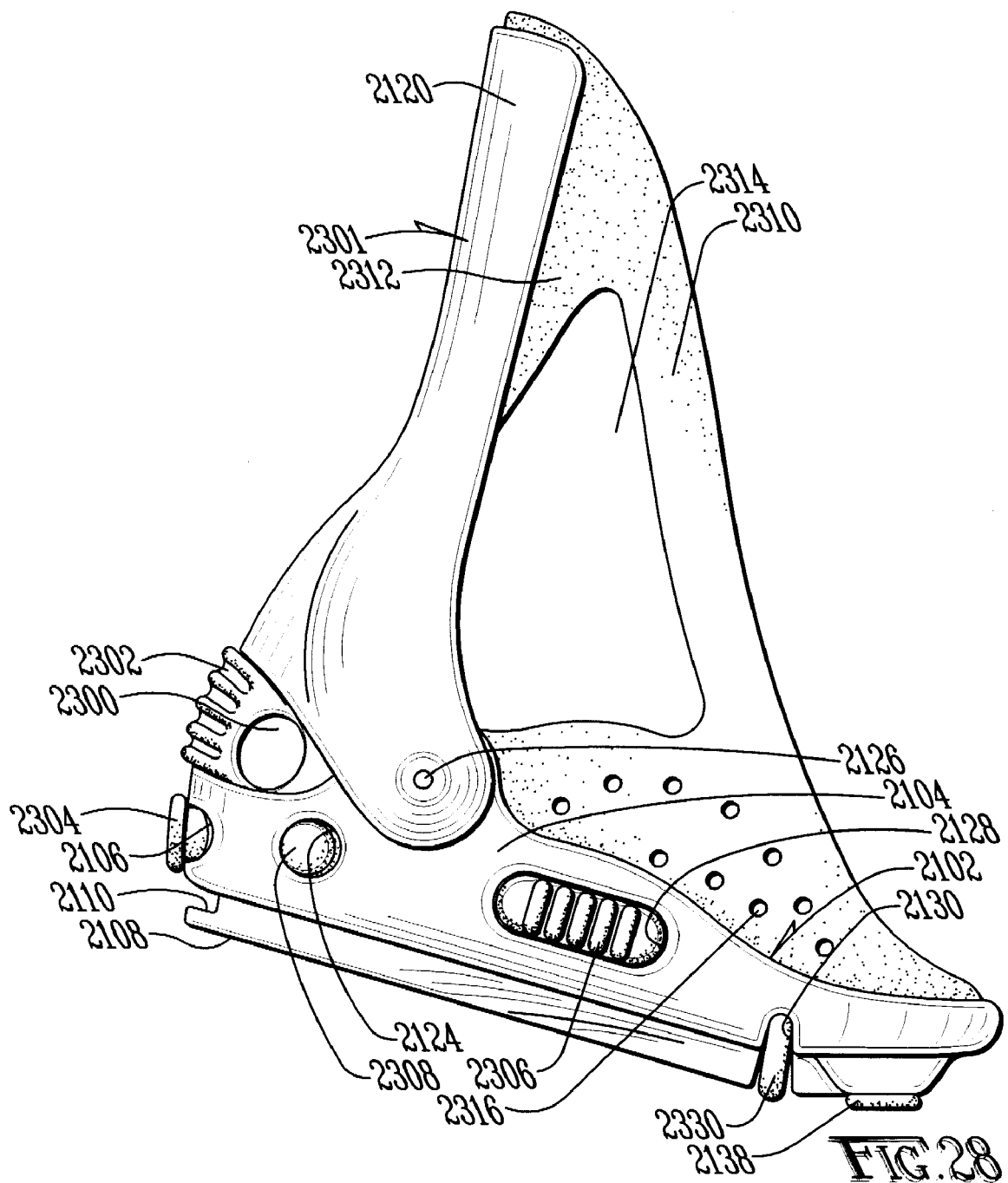
FIG. 28 is a view of the shoe of the present invention in a flexed position.

Now referring to FIG. 28, there is shown the structure of FIG. 27 where the patient is in a walking position and the top portion of the ankle foot orthosis shoe sole 2102 is flexing with respect to the heel portion. It is clear that the sole flex permitting slot 2130 is larger in FIG. 28 than in FIG. 27.

Now referring to FIG. 29, there is shown a portion of rigid bar splint assembly 2400 (FIG. 30), including first rigid bar half 2402 which is pivotally connected to first pivoting end 2408 via first rigid bar pivot connection 2405. Shoe separating setting device 2406 is used to couple first rigid bar half 2402 to second rigid bar half 2404 (FIG. 30).

Now referring to FIG. 30, there is shown a rigid bar splint assembly 2400 with second rigid bar half 2404, second rigid bar pivot connection 2407 and second pivoting end 2410, as well as second screw 2414.

The shoe separating setting device 2406 may contain a set screw or more to hold the first rigid bar half 2402 and the second rigid bar half 2404 at a set relative position.

The pivoting of first rigid bar pivot connection 2405 is better understood by referring to FIG. 31 which shows how the first pivoting end 2408 might be mounted behind the first rigid bar half 2402 and pivot around the first rigid bar pivot connection 2405, the arrow showing the rotational motion permitted in such a configuration.

Figure 32:
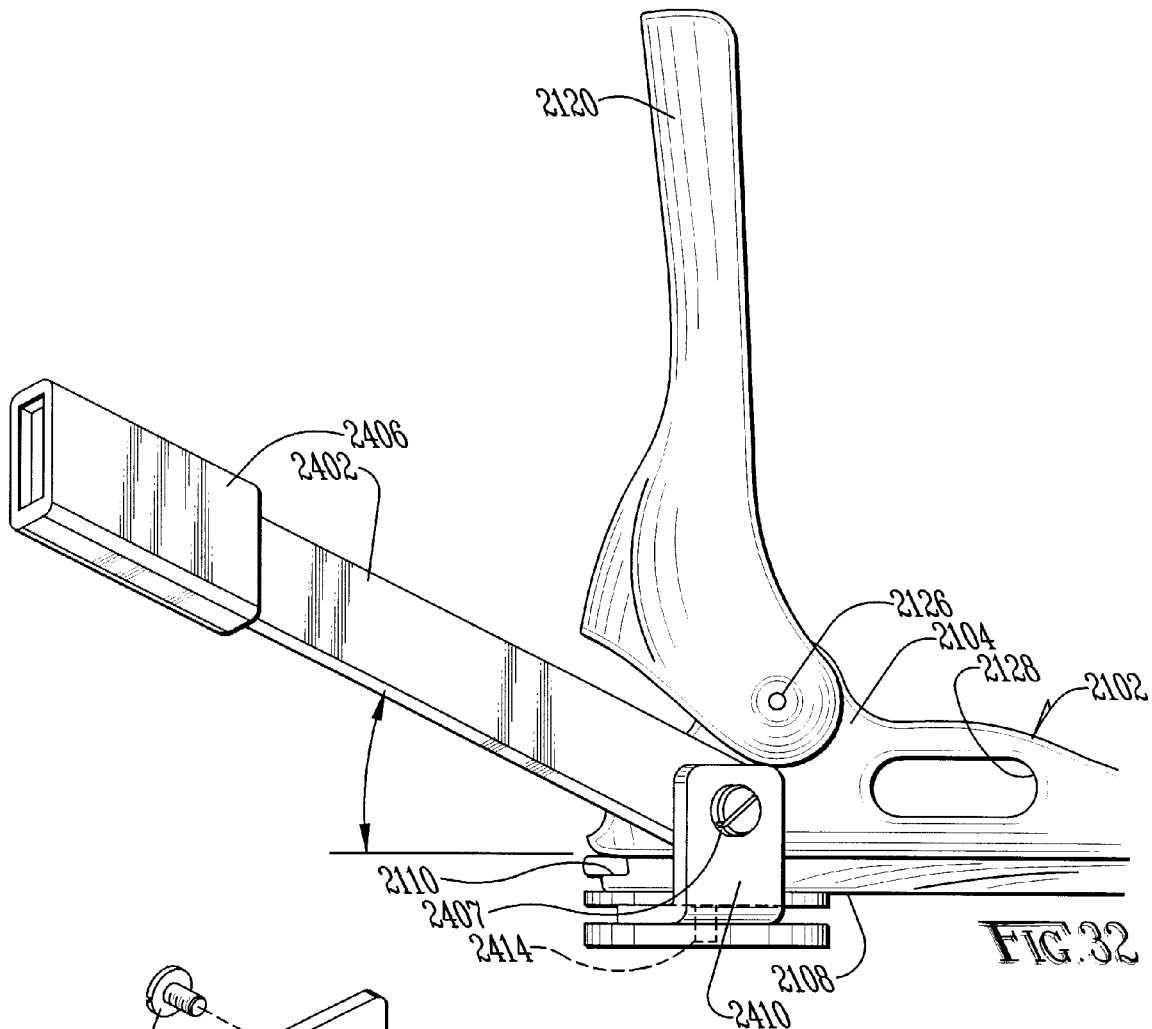
FIG. 32 is a combination of the rigid bar of FIG. 29 in combination with a structure of FIG. 17.

FIG. 32 shows the second pivoting end 2410 coupled to an ankle foot orthosis shoe sole 2102 via sub sole heel raising matter 2108.

Figure 33:
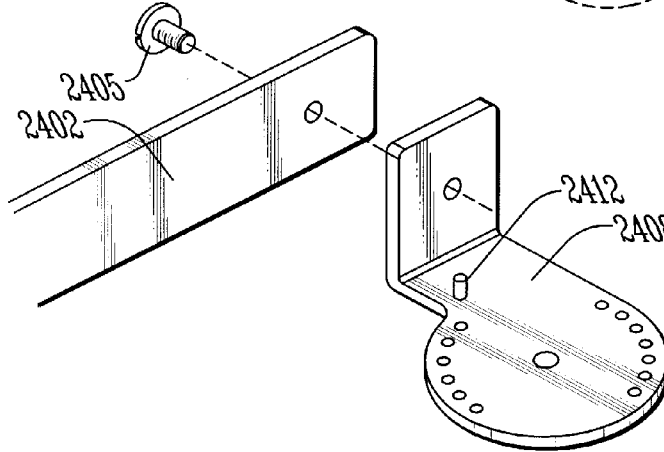
FIG. 33 is an exploded close-up view of the joint at a pivot point.

Now referring to FIG. 33, there is shown an exploded view of a first rigid bar pivot connection 2405 with a first pivoting end 2408 and a first rigid bar half 2402 on the back side of first pivoting end 2408. This alternate configuration is also possible. Note that the first rigid bar half 2402 may be more easily pivoted in a 360 degree rotation in this configuration. In fact, the first rigid bar half 2402 is shown 180 degrees pivoted with respect to the pivoting of these two pieces in FIG. 29. Various other pivoting configurations could be used as well.

First pivoting end 2408 and second pivoting end 2410 are coupled to the ankle foot orthosis shoe sole 2102 just as the bar end 1042 was attached in FIGS. 6, 7, 8 and 14. The ankle foot orthosis shoe sole 2102 is coupled to the rigid bar splint assembly 2400 in that the connections are not rigid in all directions but include first rigid bar pivot connection 2405 and second rigid bar pivot connection 2407 for limited rotational motion in predetermined planes of rotation.

Throughout this description, reference is made to the Ponseti method and to Denis Browne splints, because these methods and apparatuses are well known in the art and are believed to be the environment where the present invention would most likely be used. However, the novel aspects of the present invention could be used with other methods and in splints other than Denis Browne splints.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

I claim:

1. A foot abduction brace comprising:
a foot abduction brace bar having a right end and a left end;
a right ankle foot orthosis coupled to the right end by a first pivotal connection;
a left ankle foot orthosis coupled to the left end; and
the right ankle foot orthosis comprising a substantially rigid flexion control plate and a substantially rigid ankle foot orthosis shoe sole, coupled together in a pivotal relationship, which is independent of the first pivotal connection and remains operational while said right ankle foot orthosis is simultaneously being worn by a patient and is coupled to the right end, pivoting between the substantially rigid ankle foot orthosis shoe sole and the substantially rigid flexion control plate results in an increase or decrease in plantar flexion; and shock absorbing matter disposed between the substantially rigid flexion control plate and the substantially rigid ankle foot orthosis shoe sole so as to either restrict or urge such pivoting;
the substantially rigid flexion control plate extends above the substantially rigid ankle foot orthosis shoe sole;
said shock absorbing member comprising a pliable material and wherein shock absorbing material is a heel portion of a pliable foot cradling insert disposed on the ankle foot orthosis shoe sole.

2. The foot abduction brace of claim 1 further comprising an adjustment screw configured to adjust restrictions on an amount of variation in foot plantar flexion which is permissible while the right ankle foot orthosis is being worn by a patient and remains coupled to the right end.

3. The foot abduction brace of claim 1 wherein the right foot ankle orthosis is fixed to a first pivoting end at a predetermined angular orientation around a first axis, where the first pivoting end is freely pivotally coupled to the right end around a second axis which remains orthogonal to said first axis.

4. A foot abduction brace comprising:
a foot abduction brace bar having a right end and a left end;
a right ankle foot orthosis coupled to the right end;
a left ankle foot orthosis coupled to the left end;
the right ankle foot orthosis comprising an ankle foot orthosis shoe sole having a toe portion, a heel portion and a lateral gap therein extending entirely through and at least partially across the ankle foot orthosis shoe sole so as to permit flexing of the toe portion with respect to the heel portion, when the right ankle foot orthosis is being worn by a patient and is simultaneously coupled to said right end; and
a pliable removable one piece foot cradling insert comprising an insert sole portion opposing insert side portions and a posterior Achilles support member disposed on the ankle foot orthosis shoe sole and spanning the lateral gap so as to restrict flexing between the toe portion and the heel portion.

5. The foot abduction brace of claim 4 wherein the pliable foot cradling insert further comprises a protuberance of pliable material in registration with and at least partially disposed in the lateral gap.

6. The foot abduction brace of claim 4 wherein the pliable foot cradling insert further comprises a plurality of lateral foot drop limiting support bands.

7. The foot abduction brace of claim 6 wherein the right foot ankle orthosis further comprises a flexion control plate and a substantially rigid heel sole member.

8. A foot abduction brace comprising:
a foot abduction brace bar with a first end and a second end;
a first shoe configured to be substantially attached in one of a plurality of angular positions, around a first axis, with respect to the first end;
the first shoe comprising a first shoe heel portion, an opposing first shoe toe portion, and a first shoe sole configured to underlie and provide support for a sole of a foot when disposed in the first shoe;
a second shoe configured to be substantially attached in one of a plurality of angular positions with respect to the second end;
the second shoe comprising a second shoe heel portion, an opposing second shoe toe portion and a second shoe sole configured to underlie and provide support for a sole of a foot when disposed in the second shoe;
the second shoe configured so that the first shoe and the second shoe can be maintained in a substantially fixed relative angular orientation;
the foot abduction brace bar extending between the first shoe and the second shoe and being disposed above a point of a pivotal connection with the first shoe sole and above a point of a pivotal connection with the second shoe sole;
the foot abduction brace bar being further disposed behind the first shoe heel portion and the second shoe heel portion;
said first shoe, said second shoe, and said abduction brace bar being configured so that a straight line can always be drawn from any point on said first shoe to any point on said second shoe, which line remains in front of said foot abduction brace bar and wherein the first shoe is substantially pivotally coupled to the first end around a second axis which is substantially perpendicular to the first axis.

9. The foot abduction brace of claim 8 further comprising a pliable shoe insert comprising a pair of diagonally oriented plantar flexion inhibiting flexible members on opposing sides, the shoe insert configured to be inserted in the first shoe.

10. The foot abduction brace of claim 9 further comprising a substantially rigid plantar flexion control plate which pivots with respect to a substantially rigid portion of the second shoe.

11. The foot abduction brace of claim 10 further comprising an adjustment screw disposed in the plantar flexion control plate which is configured to limit permissible plantar flexion when the adjustment screw is moved in and out.

12. A foot abduction brace comprising:
a foot abduction brace bar having a right end and a left end;
a right ankle foot orthosis coupled to the right end in a first pivotal connection;
a left ankle foot orthosis coupled to the left end;
the right ankle foot orthosis comprising a substantially rigid flexion control plate and a substantially rigid ankle foot orthosis shoe sole coupled together in a pivotal relationship which is independent of the first pivotal connection and remains operational while said right ankle foot orthosis is simultaneously being worn by a patient and is coupled to the right end;
the substantially rigid flexion control plate extends above the substantially rigid ankle foot orthosis shoe sole;
an adjustment screw configured to adjust restrictions on permissible foot plantar flexion and further comprising shock absorbing matter disposed between the substantially rigid flexion control plate and the substantially rigid ankle foot orthosis shoe sole so as to restrict foot plantar flexion.

13. A foot abduction brace comprising:
a foot abduction brace bar with a first end and a second end;
a first shoe configured to be substantially attached in one of a plurality of angular positions, around a first axis, with respect to the first end;
the first shoe comprising a first shoe heel portion, an opposing first shoe toe portion, and a first shoe sole configured to underlie and provide support for a sole of a foot when disposed in the first shoe;
a second shoe configured to be substantially attached in one of a plurality of angular positions with respect to the second end;
the second shoe comprising a second shoe heel portion, an opposing second shoe toe portion and a second shoe sole configured to underlie and provide support for a sole of a foot when disposed in the second shoe;
the second shoe configured so that the first shoe and the second shoe can be maintained in a substantially fixed relative angular orientation;
the foot abduction brace bar extending between the first shoe and the second shoe and being disposed above a point of a pivotal connection with the first shoe sole and above a point of a pivotal connection with the second shoe sole; and
the first shoe is substantially pivotally coupled to the first end around a second axis which is substantially perpendicular to the first axis, such that a rotation limiting set screw limits rotation around said second axis.

14. The foot abduction brace of claim 13 wherein the foot abduction brace bar being further continuously disposed entirely behind the first shoe and the second shoe.

15. The foot abduction brace of claim 14 further comprising a pliable shoe insert comprising a pair of diagonally oriented plantar flexion inhibiting flexible members on opposing sides, the shoe insert configured to be inserted in the first shoe.

16. The foot abduction brace of claim 15 further comprising a substantially rigid plantar flexion control plate which pivots with respect to a substantially rigid portion of the second shoe.

17. The foot abduction brace of claim 16 further comprising an adjustment screw disposed in the plantar flexion control plate which is configured to limit permissible plantar flexion when the adjustment screw is moved in and out.

\* \* \* \* \*